June 17, 1975 H. VINCENT ET AL Plant Pat. 3,731
GLADIOLUS PLANT
Filed March 18, 1974
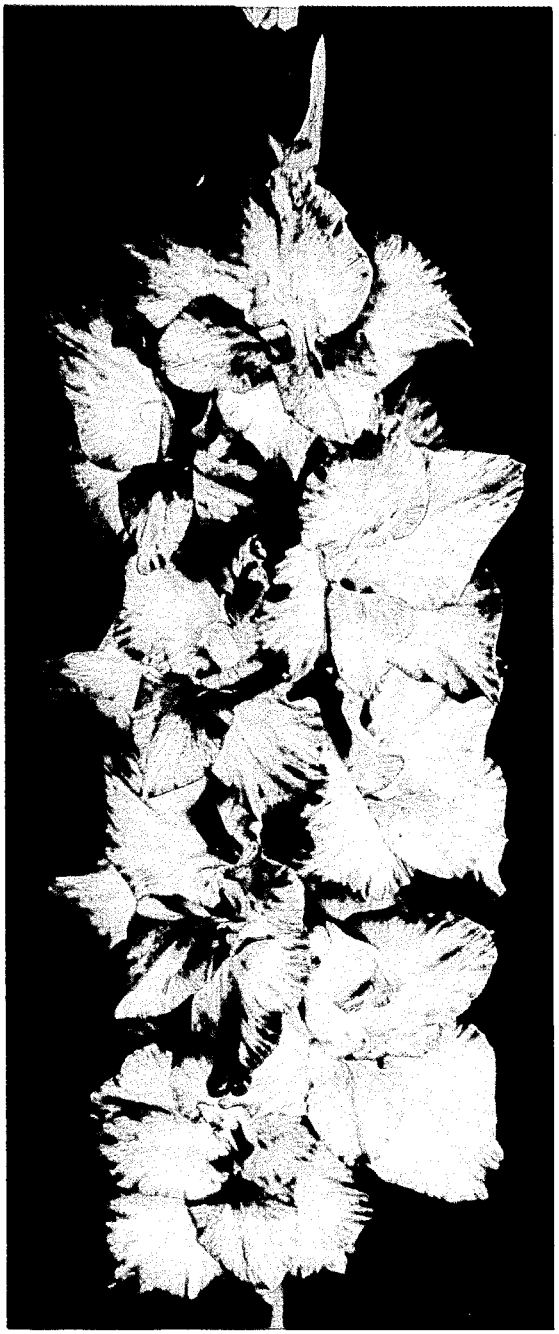

United States Patent

Plant Pat. 3,731

Patented June 17, 1975

3,731

GLADIOLUS

Harold Vincent and Herbert J. Vincent, Rock City, Ill., assignors to Selected Glads, Inc., New Albany, Ind.

Filed Mar. 18, 1974, Ser. No. 452,289

Int. Cl. A01h *5/00*

U.S. Cl. Plt.—85 1 Claim

This invention relates to a new and distinct variety of gladiolus plant.

This new gladiolus plant was originated by us by crossing the variety known as "Violet Charm/Flad Blue SLDG" with the variety known as "Blue Ribbon," "Violet Charm/Flad Blue SLDG" being the seed parent, "Blue Ribbon" being the pollen parent.

The improved variety resulting from this breeding is evidenced by the following unique combination of characteristics which are outstanding therein and which distinguish our new variety from its parents, as well as from other varieties of which we are aware:

First: An extremely robust healthy plant having tall dark green foliage, with florets of outstanding magnitude, and a height of about five feet.

Second: Dark violet colored florets.

In addition to these major characteristics our variety is also endowed with the following characteristics:

1. Good bud count opening many florets at one time
2. Consistently straight spikes
3. Long stem, yet freedom from crooking
4. Good health
5. Admirable and consistent growth habits
6. Excellent propagative powers.

We have asexually reproduced the new variety by natural increase from cormels through several generations in Illinois, and succeeding generations have established that the distinguishing characteristics of the variety held true through propagations by plantings derived from cormels.

The accompanying drawing shows a typical specimen of a flower spike of the new variety, with the flowers in varied stages of growth. Some are shown as partially opened buds and others as fully opened buds. The colors depicted are as nearly true as is possible to achieve in this type of reproduction.

The following is a detailed description of our new variety, with color terminology in accordance with the Horticultural Colour Charts issued by the British Colour Council and the Royal Horticultural Society, except where general color terms of ordinary dictionary significance are obvious.

*Plant*

Growth

Strong, healthy, excellent propagator attaining a height of 60 inches.

Blooming Habit

Comes into bloom, under normal conditions, in approximately 75–80 days, in midwestern latitudes of the United States, after planting.

Stems

*Form:* Straight.

*Diameter at base:* About ¼ inch.

*Color at base:* Dark green base of stem just above bulb.

Foliage

Above the ground leaves are dark green. The leaves of this variety are of slightly darker green than most varieties. The average leaf is two inches wide at the base, and the foliage excluding the flower spike is forty inches high.

Disease Resistance

The variety has been found to be unusually resistant to the usual gladiolus plant diseases of a bacterial, viral or fungoid genesis.

Corms

Mature bulbs are round and high crowned with heavy husks which have brownish cast.

*Color of flesh:* Salmon with a pencil line of brown where the husk is attached to the bulb.

*Flower*

Spike

*Form and size:* Straight and tall with flowerhead of 30 inches in height and regularly carrying 22 or more buds.

Bud

*Size:* About 5 inches long when opening.

*Opening:* After first blooming 6 show color at one time thereafter.

Flower

*Arrangement:* Flowerhead of the new variety has a formal placement.

*Size:* Individual florets are large, averaging about 5 inches in diameter.

*Form:* Florets are slightly rounded, the petals being slightly ruffled.

*Keeping qualities:* The flowers are long lasting and hold very well.

Petals

*Shape:* Slightly rounded.

*Size:* Upper petals being about 2⅛ inches wide. Lip petals being about 1½ inches wide.

*Aspect:* Petals are slightly rounded and lightly ruffled at edges.

*Fragrance:* None.

*Color:* Dark violet 486 at petal edges and on lip fading into lighter violet at the lightest part of upper petal. Reverse of the floret is dark violet while the sheaths and stem of the flowerhead have a dark green case.

*Reproductive Organs*

Stamens

*Color:* Medium violet.

Pistils

*Color:* White.

*Growth*

Locality where grown and observed: Rock City, Ill.

Propagation: Holds its distinguishing characteristics through succeeding propagations from cormels.

It can be seen that this variety is unique in its size, height with large florets, and in its violet color.

What we claim is:

1. A new and distinct variety of gladiolus plant, substantially as herein shown and described, characterized particularly as to novelty by the unique combination of its violet color.

No references cited.

ROBERT E. BAGWILL, Primary Examiner